US012740896B2

(12) United States Patent
Xia et al.

(10) Patent No.: US 12,740,896 B2
(45) Date of Patent: Sep. 22, 2026

(54) FLEXIBLE DEMOLDING DEVICE, CORE MOLDING DEVICE, AND CORE FORMING METHOD

(71) Applicant: SHANGHAI ZHILIAN PRECISION MACHINERY CO., LTD., Shanghai (CN)

(72) Inventors: Shuangyin Xia, Shanghai (CN); Guohong Zhou, Shanghai (CN); Guangyan Chen, Shanghai (CN)

(73) Assignee: SHANGHAI ZHILIAN PRECISION MACHINERY CO., LTD., Shanghai (CN)

( * ) Notice: Subject to any disclaimer, the term of this patent is extended or adjusted under 35 U.S.C. 154(b) by 343 days.

(21) Appl. No.: 18/552,794

(22) PCT Filed: May 18, 2021

(86) PCT No.: PCT/CN2021/094359
§ 371 (c)(1),
(2) Date: Sep. 27, 2023

(87) PCT Pub. No.: WO2022/205579
PCT Pub. Date: Oct. 6, 2022

(65) Prior Publication Data

US 2024/0225912 A1 Jul. 11, 2024

(30) Foreign Application Priority Data

Mar. 29, 2021 (CN) ......................... 202110330145.8
Mar. 29, 2021 (CN) ......................... 202110330155.1

(51) Int. Cl.
*A61F 13/15* (2006.01)
*D04H 1/732* (2012.01)

(52) U.S. Cl.
CPC .. *A61F 13/15617* (2013.01); *A61F 13/15707* (2013.01); *A61F 13/15804* (2013.01);
(Continued)

(58) Field of Classification Search
CPC .......... A61F 13/15617; A61F 13/15804; A61F 13/15707; A61F 2013/15926; D04H 1/732
See application file for complete search history.

(56) References Cited

U.S. PATENT DOCUMENTS 2,949,646 A * 8/1960 Clark .................... B27N 3/143
19/301
3,766,922 A * 10/1973 Krusko ................ A61F 13/491
604/374

(Continued)

FOREIGN PATENT DOCUMENTS

CN 1122150 A 5/1996
CN 101484106 A 7/2009

(Continued)

OTHER PUBLICATIONS

China National Intellectual Property Administration, First Office Action in CN Application No. 202110330145.8, issued Dec. 3, 2024, 13 pages with English translation.

(Continued)

*Primary Examiner* — Timothy Kennedy
(74) *Attorney, Agent, or Firm* — Schwabe, Williamson & Wyatt, P.C.

(57) ABSTRACT

A flexible demolding device, comprising a flexible substrate and a driving device. A plurality of forming holes are provided on the flexible substrate and penetrate through the thickness direction of the flexible substrate. The driving device drives the flexible substrate to move continuously in a defined direction. The driving device comprises a driving (Continued)

wheel, a supporting wheel and a conveying belt which is sleeved between the driving wheel and the supporting wheel. The flexible substrate is fixed on the conveying belt. On one hand, the demolding assembly no longer has a rigid structure. On the other hand, since the flexible substrate can be fixed on the conveying belt by means of the connecting body, the flexible substrate can be easily replaced.

14 Claims, 6 Drawing Sheets

(52) U.S. Cl.
CPC .... *D04H 1/732* (2013.01); *A61F 2013/15926* (2013.01); *A61F 2013/15991* (2013.01)

(56) References Cited

U.S. PATENT DOCUMENTS 3,846,871 A * 11/1974 Kolbach ............... A61F 13/532 19/301
3,851,356 A * 12/1974 Savich .............. A61F 13/15626 28/116
3,939,240 A * 2/1976 Savich .............. A61F 13/15626 264/109
3,973,291 A * 8/1976 Kolbach ............... A61F 13/532 19/301
4,859,388 A * 8/1989 Peterson ........... A61F 13/15626 264/517
4,892,470 A * 1/1990 Farrington ........ A61F 13/15626 425/81.1
5,118,376 A * 6/1992 Pigneul ............. A61F 13/15658 156/219
5,145,351 A * 9/1992 Rossi ................ A61F 13/15626 425/81.1
5,415,717 A * 5/1995 Perneborn ......... A61F 13/15642 118/301
5,575,874 A 11/1996 Griesbach, III
5,795,389 A * 8/1998 Koschitzky ............. B05C 19/00 118/325
7,001,167 B2 * 2/2006 Venturino ............. A61F 13/532 264/517
2003/0042660 A1 * 3/2003 Venturino ......... A61F 13/15658 264/517
2005/0167874 A1 8/2005 Larsson
2007/0246147 A1 * 10/2007 Venturino ......... A61F 13/15642 156/290
2010/0013118 A1 1/2010 Edvardsson
2011/0049758 A1 * 3/2011 Takahashi ......... A61F 13/15658 425/112
2012/0018078 A1 1/2012 Ishikawa
2012/0247349 A1 * 10/2012 Ogasawara ....... A61F 13/15658 100/90
2012/0312463 A1 12/2012 Ogasawara et al.
2013/0289509 A1 10/2013 Mukai
2014/0027943 A1 * 1/2014 Hoshika ............ A61F 13/15658 425/449
2019/0201247 A1 * 7/2019 Tsukuda ............ A61F 13/15642
2024/0148564 A1 * 5/2024 Xia ................... A61F 13/15804

FOREIGN PATENT DOCUMENTS

CN 102355877 A 2/2012
CN 202497336 U 10/2012
CN 103237532 A 8/2013
CN 103948471 A 7/2014
CN 105496649 A 4/2016
CN 105813609 A 7/2016
CN 205694955 U 11/2016
CN 107910421 A 4/2018
CN 208582599 U * 3/2019
CN 209032868 U 6/2019
CN 209474985 U 10/2019
CN 110915374 A 3/2020
CN 214572574 U 11/2021
CN 214967749 U 12/2021
EP 0256871 A2 8/1987
GB 190911380 A 4/1910
GR 871279 B 12/1987
JP H06100131 A 4/1994
WO WO-9611094 A1 * 4/1996 ............. B29C 33/42
WO 2008010753 A1 1/2008

OTHER PUBLICATIONS

European Patent Office, Extended European Search Report in EP Application No. 21934230.0, mailed Feb. 11, 2025, 5 pages.
International Search Report and Written Opinion for PCT/CN2021/094359, dated Jan. 6, 2022; 12 pages including English translation of search report.

* cited by examiner

FLEXIBLE DEMOLDING DEVICE, CORE MOLDING DEVICE, AND CORE FORMING METHOD

CROSS-REFERENCE TO RELATED APPLICATIONS

The present application is a national phase entry under 35 U.S.C. § 371 of International Application No. PCT/CN2021/094359, filed May 18, 2021 which designates the United States of America, which claims priority to CN application No. 202110330155.1, filed Mar. 29, 2021, and CN application No. 202110330145.8, filed Mar. 29, 2021, the entire disclosures of each of these applications are hereby incorporated by reference in their entireties and for all purposes.

FIELD

The present application relates to a flexible demolding device, a core molding device, and a method for forming a core.

BACKGROUND

In a disposable sanitary product, a core is a main carrier for absorbing liquid, and is generally formed by entanglement and accumulation of dispersed fluff pulp fibers.

With reference to FIG. 1 and FIG. 2, FIG. 1 and FIG. 2 show an existing apparatus for forming the core of a disposable sanitary product, which includes a molding assembly 1, a demolding cylinder 2 connected to a negative pressure system and a transfer roller 3 for transferring the core from the demolding cylinder 2 to a base material. A mold 4 with a structure corresponding to a shape of the core is fixed on the demolding cylinder 2, and the fluff pulp fibers are spread on the mold 4 by the molding assembly 1 to form the core. In this structure, the mold 4 is of a rigid structure. On the one hand, it is extremely inconvenient to manufacture, mount and use, and on the other hand, when detaching the core from the mold 4, there is likely absorbent material to be remained.

Therefore, there is a need to develop and implement a new alternative solution for the equipment, as well as a method for forming the core of the disposable sanitary product through a new device and solution.

SUMMARY

In view of this, a flexible demolding device is provided according to the present application to solve the above technical problems.

A flexible demolding device for forming a core of a disposable sanitary product includes a flexible substrate and a driving device. The flexible substrate is provided with multiple forming holes penetrating through the flexible substrate along its thickness direction. The driving device is configured to drive the flexible substrate to move continuously in a desired direction. The driving device includes a driving wheel, a supporting wheel, and a conveying belt sleeved between the driving wheel and the supporting wheel. The flexible substrate is detachably fixed on the conveying belt by means of multiple connecting bodies.

In an embodiment, the flexible substrate is connected head-to-tail along its length direction into a loop.

In an embodiment, each connecting body includes a clamping block, and multiple clamping grooves are arranged on a periphery of the driving wheel and each is positioned corresponding to the clamping block.

In an embodiment, the conveying belt is a synchronous belt including multiple first teeth, and the driving wheel includes second grooves fitted with the first teeth. A spacing between adjacent clamping grooves is greater than that between adjacent second grooves, and a depth of the clamping groove is greater than that of the second groove.

In an embodiment, the clamping block includes a first side surface facing towards a middle portion of the conveying belt, and the first side surface is obliquely arranged. The clamping groove includes a first side wall matching the first side surface, and the first side wall is also obliquely arranged.

In an embodiment, a pair of clamping blocks are provided, and the first side surfaces of the pair of clamping blocks are inclined in opposite directions and towards each other.

Beneficial effects: a flexible demolding device is provided according to the present application, which includes a flexible substrate and a driving device. The flexible substrate is provided with multiple forming holes penetrating through the flexible substrate along its thickness direction. The driving device is configured to drive the flexible substrate to move continuously in a desired direction. The driving device includes a driving wheel, a supporting wheel, and a conveying belt sleeved between the driving wheel and the supporting wheel. The flexible substrate is detachably fixed on the conveying belt by means of multiple connecting bodies. On the one hand, the demolding assembly is no longer a rigid structure. On the other hand, since the flexible substrate is fixed on the conveying belt by means of the connecting body, the flexible substrate can be easily replaced, and, when the connecting body is provided with a protrusion and the driving wheel is provided with a corresponding clamping groove, the size precision of the forming holes on the flexible substrate can be easily maintained.

A core molding device using the flexible demolding device is further provided according to the present application, which includes a molding assembly and a suction assembly.

The molding assembly includes a cavity and a spreading port configured for spreading the absorbent material.

The suction assembly includes a suction area connected to a negative pressure system. The suction area and the spreading port are spaced apart from and opposite to each other.

When the flexible substrate having the forming holes is moved to between the spreading port and the suction area, the molding assembly fills the absorbent material into the forming holes of the flexible substrate through the spreading port to form a web tissue corresponding to the shape of the forming hole.

In an embodiment, the suction assembly further includes a holding device. The holding device includes at least one holding surface, so that the holding surface and the forming hole together form a forming cavity with the holding surface as a bottom part and the side wall of the forming hole as a wall part, and thus the absorbent material can be filled into the forming cavity to form a web tissue. The holding surface is a flat surface or a curved surface.

In an embodiment, the holding device includes a holding mesh, and the holding surface is a side surface of the holding mesh facing towards the spreading port.

In an embodiment, a web material laying assembly is further arranged upstream of the suction assembly for conveying the web material on the suction assembly. The web material is a porous mesh sheet and is configured to be conveyed between the spreading port and the suction area. The flexible substrate is superposed on the web material, and the holding surface is a side surface of the web material facing towards the spreading port.

In an embodiment, the suction assembly includes a suction cavity. The suction cavity includes an opening portion, and the opening portion includes a suction surface including a suction area and a detaching area. The suction area is arranged corresponding to the spreading port, and the detaching area is arranged downstream of the spreading port and not corresponding to the spreading port. The flexible substrate is separated from the suction surface in the detaching area.

In an embodiment, the shape of the forming hole is in a regular or irregular pattern, and the core has an outline shape matching the shape of the forming hole.

In addition, a method for forming a core is further provided according to the present application, which includes providing the core molding device and the absorbent material described above, continuously passing the flexible substrate over the spreading port, and filling, by the molding assembly, the absorbent material into the forming hole through the spreading port to form a web tissue corresponding to the shape of the forming hole when the flexible substrate having the forming hole is moved to between the spreading port and the suction area.

In an embodiment, the method further includes a step of dispersing the absorbent material and a step of laying the web material on the suction assembly before the molding assembly fills the absorbent material into the forming hole through the spreading port.

Beneficial effects: a core molding device is provided according to the present application, which includes a molding assembly, a flexible demolding device and a suction assembly. The molding assembly includes a cavity and a spreading port. The suction assembly includes a suction area. The suction area and the spreading port are spaced apart from and opposite to each other. The flexible demolding device includes a flexible substrate provided with forming holes and a driving device. When the flexible substrate provided with the forming holes is moved to between the spreading port and the suction area, the molding assembly fills the absorbent material into the forming holes through the spreading port to form a web tissue corresponding to the shape of the forming hole. On the one hand, the demolding assembly is no longer a rigid structure, which greatly reduces the manufacturing difficulty and modifying difficulty. On the other hand, the forming holes are arranged on the movable flexible substrate, and the core does not need to be transferred by the transfer roller after formed, thus avoiding an occurrence of residual absorbent material during a secondary transfer by the transfer roller. Correspondingly, a method for forming the core is further provided according to the present application.

Figure 1:
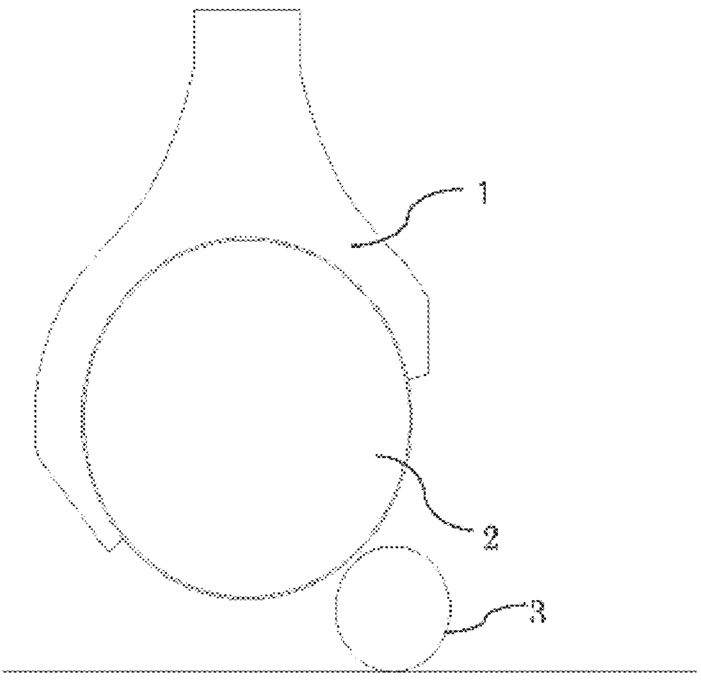
FIG. 1 is a schematic view showing a device for forming a core of a disposable sanitary product in the conventional technology.
Figure 2:
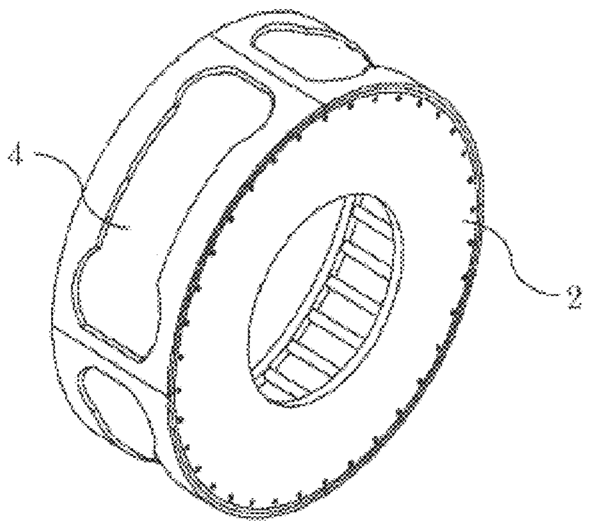
FIG. 2 is a schematic perspective view of a demolding cylinder shown in FIG. 1.

Reference numerals in the drawings are listed as below:

1, 10 molding assembly; 2 demolding cylinder; 3 transfer roller; 4 mold;

101, 301 spreading port; 102 cavity; 103 finishing device;

11 flexible demolding device; 111, 311 flexible substrate; 1110 forming hole;

112 driving device; 1121 driving wheel; 11211 clamping groove; 1122 supporting wheel; 1123 conveying belt; 1130 connecting body; 113 clamping block; 114 screw; 2210 first side surface; 2211 first side wall;

12, 32 suction assembly; 121, 321 suction cavity; 1211, 3211 suction area; 1212, 3212 detaching area; 122 holding device;

13 web material laying assembly; 131, 331 web material;

15 absorbent material;

322 cylinder wall; 3220 suction hole.

DETAILED DESCRIPTION OF THE EMBODIMENTS

Figure 3:
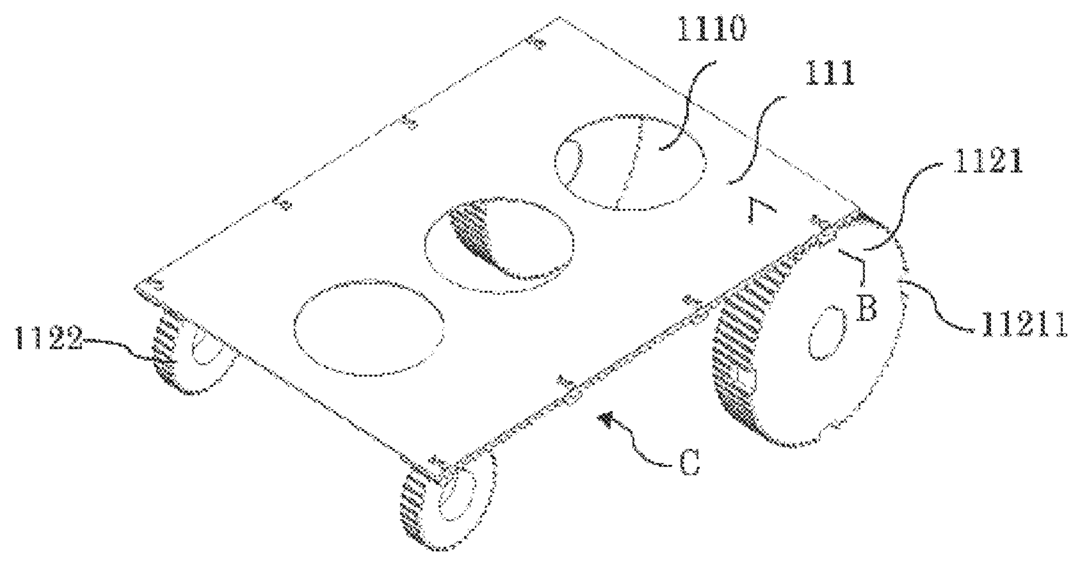
FIG. 3 is a schematic view of a flexible demolding device according to an embodiment of the present application.
Figure 4:
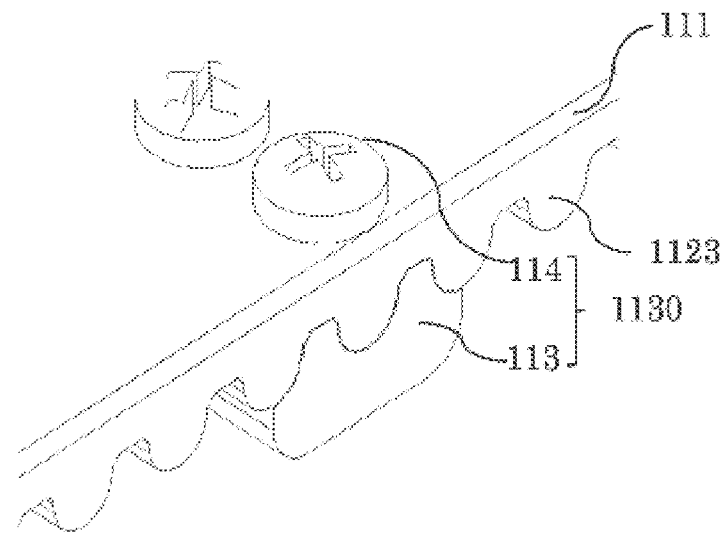
FIG. 4 is an enlarged schematic view of area C shown in FIG. 3.
Figure 5:
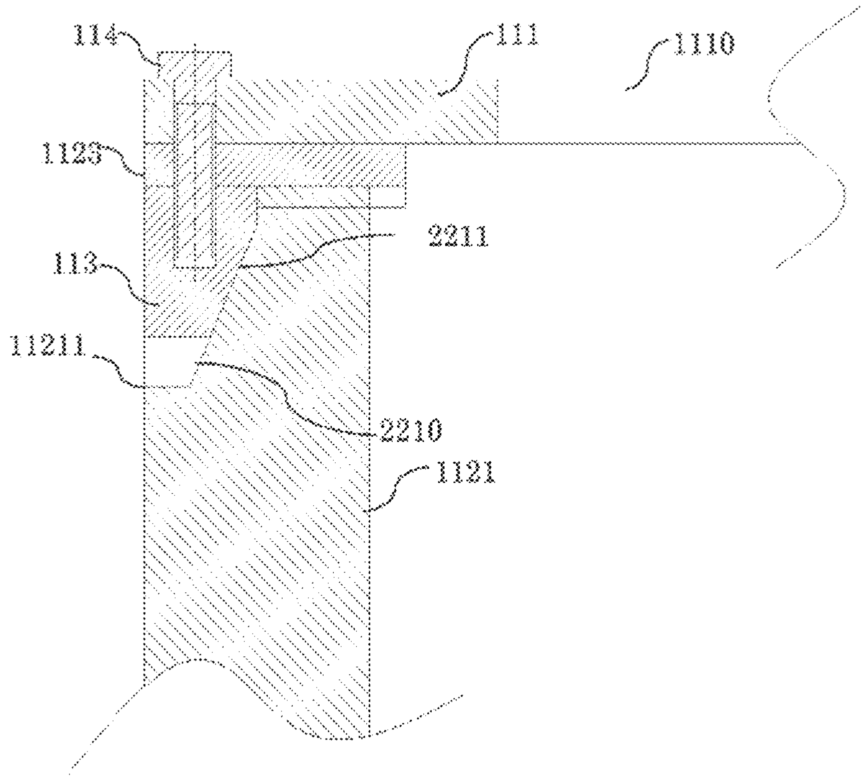
FIG. 5 is an enlarged sectional view taken along line B-B shown in FIG. 3.

With reference to FIG. 3 to FIG. 5, FIG. 3 is a schematic view showing a flexible demolding device, and FIG. 4 to FIG. 5 show structures of the flexible demolding device at corresponding positions respectively. The present application will be further described hereinafter with reference to the drawings.

First Embodiment

Provided are a flexible demolding device and a core molding device according to a first embodiment of the present application. The flexible demolding device is generally applied to the core molding device for forming a core of a disposable sanitary product, and the flexible demolding device includes a flexible substrate 111 and a driving device 112.

The flexible substrate 111 is provided with at least one forming hole 1110 penetrating through the flexible substrate 111 along its thickness direction. The driving device 112 is configured for driving the flexible substrate 111 to move continuously in a desired direction.

The forming hole 1110 is arranged on the flexible substrate 111, and the forming hole 1110 has an outline shape and a size matching the shape of the core to be formed. In this embodiment, the core is only shown in a circular shape, and other suitable shapes, such as ellipse, oval, waist, polygon and other regular or irregular shapes, can be set as required, which will not be limited herein.

Figure 6:
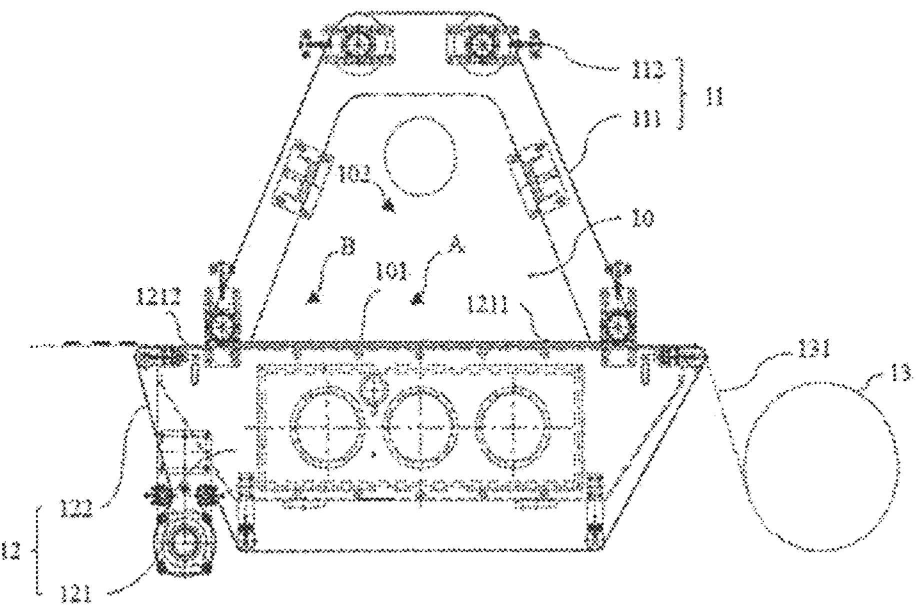
FIG. 6 is a schematic view of a core molding device according to a first embodiment of the present application.
Figure 7:
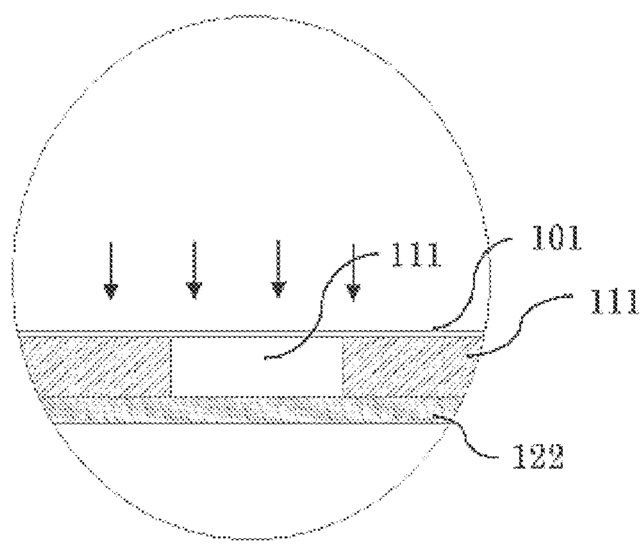
FIG. 7 is an enlarged schematic view of area A shown in FIG. 6.
Figure 8:
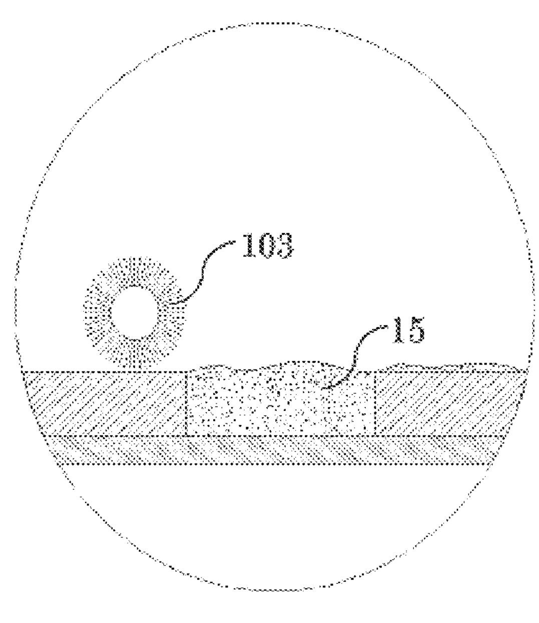
FIG. 8 is an enlarged schematic view of area B shown in FIG. 6.

With reference to FIG. 6 to FIG. 8, FIG. 6 shows the core molding device provided according to an embodiment of the present application, and FIG. 7 to FIG. 8 show structures of the core molding device at corresponding positions respectively. The present application will be further described hereinafter with reference to the drawings.

The core molding device provided according to the embodiment of the present application includes a molding assembly 10, a suction assembly 12 and a flexible demolding device 11.

Each part of the core molding device will be described in detail below.

1. Flexible Demolding Device

The flexible demolding device 11 in this embodiment adopts the flexible demolding device 11 provided according to the present application. The structures and reference numbers not mentioned are the same as those in the previous paragraphs, and will not be repeated here.

The flexible demolding device 11 includes a flexible substrate 111 and a driving device 112. The driving device includes a driving wheel 1121, a supporting wheel 1122 and a conveying belt 1123 sleeved between the driving wheel 1121 and the supporting wheel 1122. The flexible substrate 111 is connected to the conveying belt 1123.

In this embodiment, the flexible substrate 111 includes a length direction and a width direction and is connected head-to-tail along its length direction into a loop, so that the driving device can continuously drive the conveying belt 1123 and the flexible substrate 111 connected to the conveying belt 1123 to move continuously. It can be understood that the flexible substrate 111 is of a flexible structure, and thus can be set into a required shape as required, such as an annular shape composed of curves and straight lines or an annular shape composed of curves with different curvatures.

It can be understood that the flexible substrate 111 may be detachably or non-detachably connected to the conveying belt 1123.

In an embodiment, the flexible substrate 111 is detachably fixed on the conveying belt 1123 by multiple connecting bodies 1130, each of which includes a clamping block 113 and a screw 114. The clamp block 1130 includes a clamping surface fitted with the conveying belt 1123, and the screw 114 is threaded onto the clamping block 113 by passing through the flexible substrate 111 and the conveying belt 1123, so that the flexible substrate 111 and the conveying belt 1123 are connected with each other into a whole, and while the conveying belt 1123 moves, the flexible substrate 111 moves synchronously.

It can be understood that the clamping block 113 may also be fixed on the conveying belt 1123 via other means, such as a buckle or a clamp, and connect the conveying belt 1123 with the flexible substrate 111 into a whole.

The clamping block 113 protrudes on the conveying belt 1123. Multiple clamping grooves 11211 are arranged on a periphery of the driving wheel 1121 and each is positioned corresponding to the clamping block 113. On the one hand, when the driving wheel 1121 drives the conveying belt 1123, the clamping block 113 will not interfere. On the other hand, since the flexible substrate 111 is fixed on the conveying belt 1123, an actual size of the forming hole 1110 on the flexible substrate 111 may change in a case that a length of the conveying belt 1123 changes unexpectedly, and since the position of the clamping groove 11211 on the driving wheel 1121 will not change, a spacing between the clamping blocks 113 may change in a case that the length of the conveying belt 1123 changes unexpectedly, as a result of which the clamping block 113 can no longer stably fall into the clamping groove 11211, indicating that the conveying belt 1123 needs maintenance. Therefore, the size precision of the forming hole 1110 on the flexible substrate 111 can be maintained.

It can be understood that in some other embodiments, the conveying belt 1123 is further provided with a bump (not shown) which is integrally formed with the conveying belt 1123, and the bump or the clamping block 113 is positioned corresponding to the clamping groove 11211.

In an embodiment, the conveying belt 1123 is a synchronous belt and includes multiple first teeth and first grooves. The driving wheel 1121 includes multiple second teeth fitted with the first grooves respectively and second grooves fitted with the first teeth respectively. The driving wheel 1121 drives the conveying belt and the flexible substrate 111 connected with the conveying belt 1123 to move by means of the first teeth and the second grooves and the second teeth and the first grooves. The clamping grooves 11211 are arranged on the periphery of the driving wheel 1123, and the spacing between adjacent clamping grooves 11211 is greater than the spacing between adjacent second grooves.

In an embodiment, a depth of the clamping groove 11211 is greater than that of the second groove. The driving wheel 22 has a first width which is approximately equal to a width of the second tooth. A width of the clamping groove 11211 is less than or equal to ½ of the first width.

It can be understood that in this embodiment, the clamping surface is fitted with the first teeth and the first grooves, so that the clamping block 113 can be reliably and stably fixed on the conveying belt 1123.

In an embodiment, the driving device includes a pair of conveying belts 1123. A pair of clamping blocks 113 are respectively arranged on two sides of the flexible substrate 111 for connecting two sides of the flexible substrate 111 to the pair of conveying belts 1123. The conveying belt 1123 includes a middle portion, and the clamping block 113 includes a first side surface 2210 facing towards the middle portion. The first side surface 2210 is inclined such that the clamping block 113 is in a trapezoidal shape. The first side surfaces 2210 of the pair of clamping blocks 113 are inclined in opposite directions. For example, in this embodiment, the clamping block 113 located on a left side is inclined towards a lower left part, and the clamping block 113 located on a right side is inclined towards a lower right part, so that the first side surfaces 2210 of the pair of clamping blocks 113 are inclined towards each other. A pair of clamping grooves 11211 arranged on the driving wheel 1121 has first side walls 2211 matching the first side surfaces 2210 respectively. Similarly, the first side wall 2211 is also obliquely arranged, and the respective first side surface 2210 and the corresponding first side wall 2211 have a same inclination direction. It can be understood that when the flexible substrate 111 has a position deviation in a horizontal direction, since the first side surface 2210 and the first side wall 2211 are obliquely arranged, the clamping block 113 automatically moves downward along the inclination direction of the first side surface 2210 and the first side wall 2211 under an action of tension, so that the conveying belt 1123 is attached to the driving wheel 1121 and displaced in a lateral direction to reach a predetermined position. That is, the flexible substrate 111 can always be maintained in an accurate lateral position, so that the lateral position of the formed core remains constant.

In an embodiment, the first side surfaces 2210 of the clamping blocks 113 have a same inclination angle relative to a vertical direction.

In an embodiment, the inclination angle of the first side surface 2210 of each clamping block 113 relative to the vertical direction is between 30° and 60°.

It can be understood that the supporting wheel 1122 should be arranged to avoid the clamping block 113, so as to prevent the clamping block 113 from interfering with the movement of the supporting wheel 1122. In an embodiment, a width of the supporting wheel 1122 is smaller than that of the driving wheel 1121. In other embodiments, the supporting wheel 1122 may also be arranged to have a same structure as the driving wheel 1121.

In an embodiment, multiple supporting wheels 1122 may be provided, at least including the supporting wheels 1122 arranged upstream of the molding assembly 1 and the supporting wheels 1122 arranged downstream of the molding assembly 1. At least a part of the flexible substrate 111 is sleeved between the upstream supporting wheels 1122 and the downstream supporting wheels 1122, and this part of the flexible substrate 111 between the upstream supporting wheels 1122 and the downstream supporting wheels 1122 is passed over the spreading port. When the driving device drives the flexible substrate 111 to move, the absorbent material can be spread into the forming hole 1110 on the flexible substrate 111 through the spreading port, thus forming a core with a same shape as the forming hole 1110. It can be understood that the part of the flexible substrate 111 can be defined in a predetermined shape, such as a flat surface or a curved surface, which will not be limited herein.

In an embodiment, the flexible demolding device 11 further includes a finishing device 103 for forming cores with generally the same height through finishing. In this embodiment, the finishing device 103 is arranged in the cavity 102 and includes a free end abutting against an inner surface of the flexible substrate 111.

In an embodiment, the finishing device 103 includes a circular section to form a better core surface while reducing wear.

In an embodiment, the finishing device 103 is a cylindrical brush, which includes a cylinder body and multiple bristles fixed on the cylinder body. At least a part of the bristles face towards the suction area and abut against the inner surface of the flexible substrate 111 or reserve only a small gap with the inner surface of the flexible substrate 111. When rotating, the cylindrical brush cleans the surface of the flexible substrate 111, allowing the formed core to have a flat upper surface.

2. Molding Assembly

The molding assembly 10 includes a cavity 102 and a spreading port 101 configured for spreading the absorbent material 15.

The shape of the cavity 102 can be constructed according to actual needs, and will not be limited herein.

The absorbent material 15 may be fiber, such as fluff pulp fiber or man-made fiber or other suitable fiber material, or a mixture of fiber and super absorbent polymer (SAP).

Specifically, a fiber dispersing device and a conveying device are arranged upstream of the molding assembly 10 to convey the absorbent material 15, such as fiber or a mixture of fiber and super absorbent polymer, into the cavity 102. In an embodiment, the conveying device is an air conveying device to enable the cavity 102 to be in a positive pressure state and allow the absorbent material 15 to be easily spread through the spreading port 101.

3. Suction Assembly

The suction assembly 12 includes a suction area 1211 connected to a negative pressure system. The suction area 1211 and the spreading port 101 are spaced apart from and opposite to each other.

In this embodiment, the suction assembly 12 includes a suction cavity 121 which is connected to a negative pressure system to enable a negative pressure to be formed in the suction cavity 121. The suction area 1211 is formed by the suction cavity 121. In an area between the suction area 1211 and the spreading port 101, an airflow flows from the spreading port 101 towards the suction area 1211, and when the absorbent material 15 is contained in the airflow, the absorbent material 15 moves with the airflow from the spreading port 101 towards the suction area 1211.

The forming hole 1110 penetrates through the flexible substrate 111 along its thickness direction. When the part, having the forming hole 1110, of the flexible substrate 111 moves to the area between the spreading port 101 and the suction area 1211, the molding assembly 10 spreads the absorbent material 15 through the spreading port 101. Since the airflow moves from the spreading port 101 towards the suction area 1211, the airflow carries the absorbent material 15 through the forming hole 1110 towards the suction area 1211, and fills the absorbent material 15 into the forming hole 1110 to form a core structure matching the outline shape and size of the forming hole 1110 and matching the thickness of the flexible substrate 111.

In an embodiment, in order to prevent the absorbent material 15 from directly passing through the forming hole 1110, the suction assembly 12 further includes a holding device 122. The holding device 122 includes at least one holding surface, so that the holding surface and the forming hole 1110 together form a forming cavity with the holding surface as a bottom part and the side wall of the forming hole 1110 as a wall part, and thus the absorbent material 15 can be filled into the forming cavity to form a web tissue. In a specific embodiment, the holding surface may be a holding mesh or an upper surface of a web material 131.

It can be understood that the holding surface includes a suction hole allowing the airflow to pass through, and an aperture of the suction hole is matched with the size of the absorbent material 15, so as to reduce the amount of loss of the absorbent material 15 passing through the suction hole, thereby improving an efficiency of forming the core.

In an embodiment, the holding device 122 includes a holding mesh, and the holding surface is a side surface of the holding mesh facing towards the spreading port 101. In this embodiment, the holding mesh is configured to move continuously, and has the moving direction and speed as the flexible substrate 111.

In an embodiment, the holding surface is a flat surface or a curved surface.

In some other embodiments, a web material laying assembly 13 is further arranged upstream of the suction assembly 12 for conveying the web material 131 onto the suction assembly 12 to directly form the core on the web material 131, without additionally providing a transfer device to transfer the core to the web material 131.

Specifically, the web material 131 is configured to be conveyed between the spreading port 101 and the suction area 1211, and the flexible substrate 111 is superposed on the web material 131, thus forming a forming cavity with the web material 131 as the bottom part and the side wall of the forming hole 1110 as the wall part. It can be understood that, in this case, the holding surface is a side surface of the web material 131 facing towards the spreading port 101, and the web material 131 is a porous mesh sheet to enable the airflow to pass through the web material 131. The web material 131 may be non-woven fabric, toilet paper and the like, which will not be limited herein.

The driving device 112 is used to drive the flexible substrate 111 to move continuously to pass through the spreading port 101 continuously.

In an embodiment, the forming holes 1110 are distributed along the length direction of the flexible substrate 111. When the flexible substrate 111 continuously passes through the spreading port 101, the spreading port 101 is able to continuously form the core in the forming hole 1110 on the flexible substrate 111 at a corresponding area.

In an embodiment, in order to stably detach the formed core from the flexible substrate 111, the suction cavity 121 includes an opening portion including a suction area 1211 and a detaching area 1212. The suction area 1211 is arranged corresponding to the spreading port 101, and the detaching area 1212 is arranged downstream of the spreading port 101 and not corresponding to the spreading port 101. The meaning of "not corresponding to" means that a projection of the spreading port 101 on the holding surface is not overlapped with a projection of the suction area 1211 on the holding surface, so that the core in the detaching area 1212 is kept attached to the holding surface under the negative pressure of the suction cavity 121, while the flexible substrate 111 in the detaching area 1212 is separated from the suction surface, and the core is detached from the flexible substrate 111 under the negative pressure. When the holding surface moves in a downstream direction, the core moves in the downstream direction with the holding surface, thus continuously forming the core and conveying it downstream.

Second Embodiment

Figure 9:
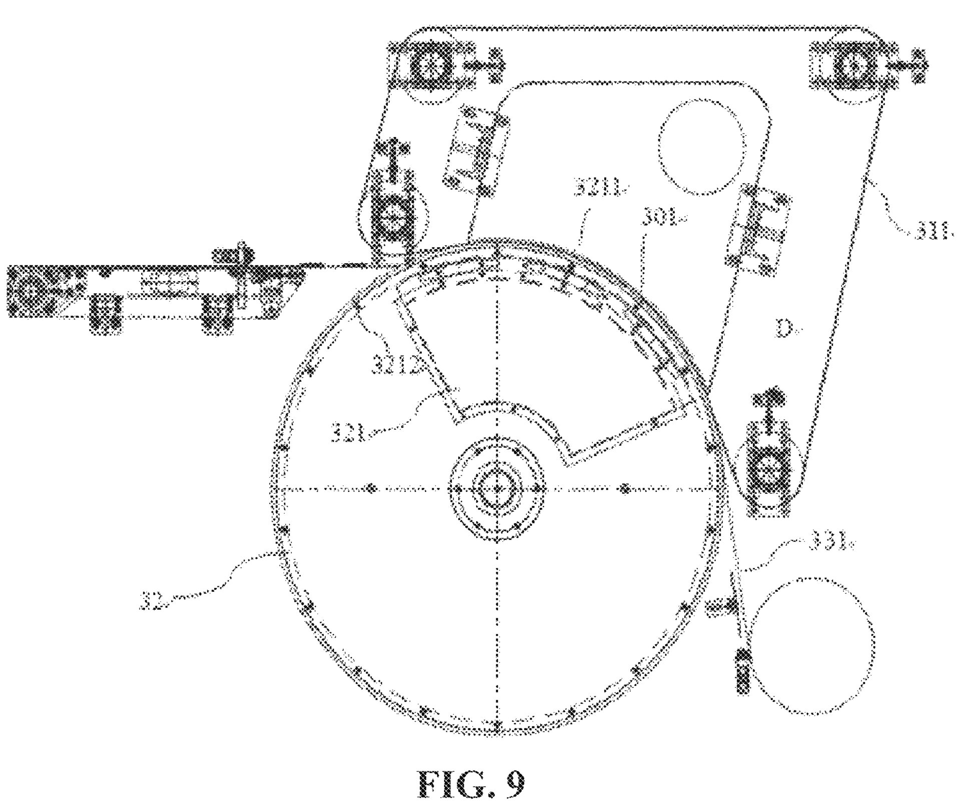
FIG. 9 is a schematic view of a core molding device according to a second embodiment of the present application.
Figure 10:
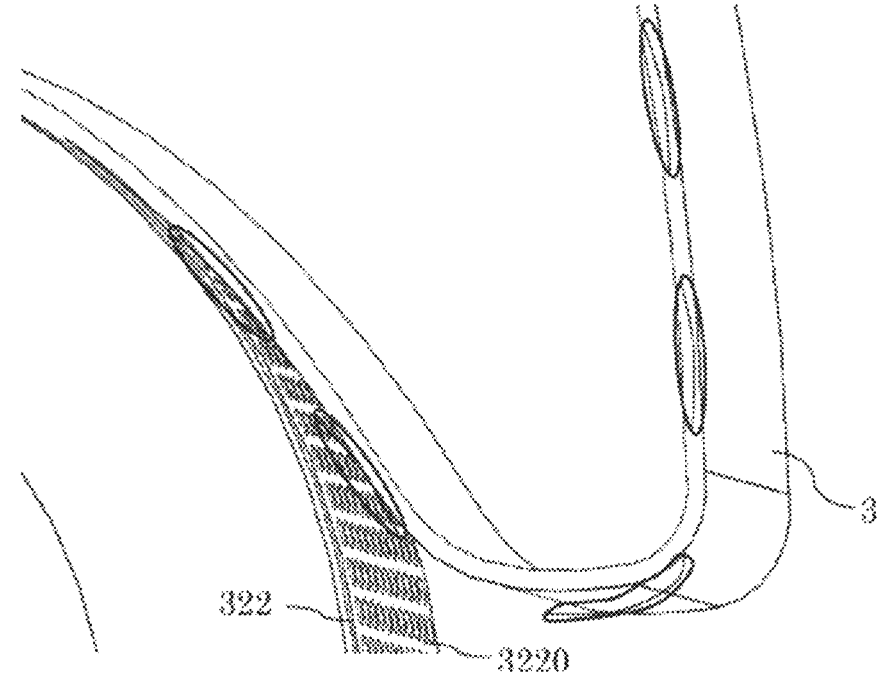
FIG. 10 is a schematic structural view of area D shown in FIG. 9.

With reference to FIG. 9 and FIG. 10, FIG. 9 and FIG. 10 show schematic views of a core molding device according to a second embodiment of the present application. In the second embodiment, the suction assembly 32 includes a suction cylinder including a cylinder wall 322. The cylinder wall 322 holds the web material 331 or directly holds the flexible substrate 311. It can be understood that in this embodiment, the suction cylinder serves as the holding device. An outer surface of the cylinder wall 322 facing towards the spreading port 301 forms the holding surface, and the suction cavity is arranged in a cylinder body of the suction cylinder. The cylinder wall 322 is provided with multiple suction holes 3220 for forming the suction area 3211.

It can be understood that in this embodiment, the suction area 3211 is a curved surface, and the spreading port 301 is also configured to be a curved surface. Similarly, the suction area 3211 is arranged to be spaced apart from the spreading port 301, so that the space between the suction area 3211 and the spreading port 301 is an arc gap.

In an embodiment, since the suction cylinder serves as the holding device, the detaching area 3212 located downstream of the suction area 3211 is also a curved surface. Since the flexible substrate 311 is wound around the supporting wheels spaced apart from each other, the flexible substrate 311 between the supporting wheels is in a linear form in a case that it is not affected by external force, that is, the flexible substrate 311 in the detaching area 3212 extends in the linear form towards the downstream supporting wheel, so that in the detaching area, the flexible substrate 311 is gradually separated from the suction surface, and thus the core can be easily detached from the flexible substrate 311.

It can be understood that in this embodiment, the holding surface is a rigid surface, thus forming a more stable support, and the suction assembly 32 rotates around an axis, allowing the movement more stable and improving the reliability of the device.

A method for forming the core of the disposable sanitary product is further provided according to the present application, which includes providing the core molding device and absorbent material 15 described above for forming the core of the disposable sanitary product, continuously passing the flexible substrate 111 over the spreading port 101, and filling the absorbent material 15 into the forming hole 1110, located at the spreading port 101, of the flexible substrate 111 through the spreading port 101 to form a web tissue corresponding to the shape of the forming hole 1110.

It can be understood that the method further includes a step of dispersing the absorbent material 15 before the absorbent material 15 is spread into the forming hole 1110, located at the spreading port 101, of the flexible substrate 111 to form the core corresponding to the shape of the forming hole 1110. The dispersing of the absorbent material 15 may be specifically crushing and air-entraining the raw material of the absorbent material 15, such as crushing the fluff pulp board by a pulverizer to form dispersed fluff pulp fibers.

In an embodiment, the method further includes a step of laying the web material 131 on the suction assembly 12 before spreading the absorbent material 15 into the forming hole 1110, located at the spreading port 101, of the flexible substrate 111 to form the core corresponding to the shape of the forming hole 1110.

In an embodiment, after spreading the absorbent material 15 into the forming hole 1110, located at the spreading port 101, of the flexible substrate 111 to form the core corresponding to the shape of the forming hole 1110, the method further includes a step of detaching the core from the flexible substrate 111.

Only preferred embodiments of the present application are described herein with no limitation on the scope of protection of the present application. Any equivalent structure or process from the specification and the drawings of the present application, or direct or indirect application in other related fields, is equally covered by the scope of protection of the present application.

The invention claimed is:

1. A flexible demolding device for forming a core of a disposable sanitary product, comprising:

a flexible substrate; and a driving device, wherein the flexible substrate is provided with a plurality of forming holes running through the flexible substrate along a thickness direction of the flexible substrate; and the driving device is configured to drive the flexible substrate to move continuously in predetermined direction, the driving device comprises a driving wheel, a supporting wheel, and a conveying belt sleeved between the driving wheel and the supporting wheel, a projection of the forming holes and a projection of the conveying belt in the thickness direction of the flexible substrate are non-overlapping, and the flexible substrate is fixed on the conveying belt.

2. The flexible demolding device according to claim 1, wherein the flexible substrate is detachably fixed on the conveying belt by means of a plurality of connecting bodies, and the flexible substrate is connected head-to-tail along its length direction into a loop.

3. The flexible demolding device according to claim 2, wherein each connecting body comprises a clamping block, and a plurality of clamping grooves are arranged on a periphery of the driving wheel and each is positioned corresponding to the clamping block.

4. The flexible demolding device according to claim 3, wherein the conveying belt is a synchronous belt comprising a plurality of first teeth, and the driving wheel comprises second grooves fitted with the first teeth, and wherein a spacing between adjacent clamping grooves is greater than that between adjacent second grooves, and a depth of the clamping groove is greater than that of the second groove.

5. The flexible demolding device according to claim 3, wherein the clamping block comprises a first side surface facing towards a middle portion of the conveying belt, and the first side surface is obliquely arranged; the clamping groove comprises a first side wall matching the first side surface, and the first side wall is also obliquely arranged.

6. The flexible demolding device according to claim 5, wherein a pair of clamping blocks are provided, and the first side surfaces of the pair of clamping blocks are inclined in opposite directions and towards each other.

7. A core molding device comprising the flexible demolding device according to claim 1, further comprising a molding assembly and a suction assembly, wherein the molding assembly comprises a cavity and a spreading port configured for spreading an absorbent material;

the suction assembly comprises a suction area connected to a negative pressure system, wherein the suction area and the spreading port are spaced apart from and opposite to each other; when the flexible substrate, having the forming holes, of the flexible demolding device is moved to between the spreading port and the suction area, the molding assembly fills the absorbent material into the forming holes of the flexible substrate through the spreading port to form a web tissue corresponding to the shape of the forming hole.

8. The core molding device according to claim 7, wherein the suction assembly further comprises a holding device, wherein the holding device comprises at least one holding surface, so that the holding surface and the forming hole together form a forming cavity with the holding surface as a bottom part and the side wall of the forming hole as a wall part, allowing the absorbent material to be filled into the forming cavity to form the web tissue, and wherein the holding surface is a flat surface or a curved surface.

9. The core molding device according to claim 8, wherein the holding device comprises a holding mesh, and the holding surface is a side surface of the holding mesh facing towards the spreading port.

10. The core molding device according to claim 8, wherein a web material laying assembly is further arranged upstream of the suction assembly for conveying a web material on the suction assembly, wherein the web material is a porous mesh sheet and is configured to be conveyed between the spreading port and the suction area, the flexible substrate is superposed on the web material, and the holding surface is a side surface of the web material facing towards the spreading port.

11. The core molding device according to claim 7, wherein the suction assembly comprises a suction cavity, wherein the suction cavity comprises an opening portion, and the opening portion comprises a suction surface comprising the suction area and a detaching area, wherein the suction area is arranged corresponding to the spreading port, and the detaching area is arranged downstream of the spreading port and not corresponding to the spreading port, and wherein the flexible substrate is separated from the suction surface in the detaching area.

12. The core molding device according to claim 7, wherein the shape of the forming hole is in a regular or irregular pattern, and the core has an outline shape matching the shape of the forming hole.

13. A method for forming a core, comprising: providing the core molding device and the absorbent material according to claim 7, continuously passing the flexible substrate over the spreading port, and filling, by the molding assembly, the absorbent material into the forming hole through the spreading port to form the web tissue corresponding to the shape of the forming hole when the forming hole is moved to between the spreading port and the suction area.

14. The method for forming a core according to claim 13, further comprising a step of dispersing the absorbent material and a step of laying the web material on the suction assembly before the molding assembly fills the absorbent material into the forming hole through the spreading port.

* * * * *